(12) United States Patent
Perraudin (10) Patent No.: US 9,555,081 B2
(45) Date of Patent: *Jan. 31, 2017

(54) ANTIMICROBIAL COMPOSITION AND USES THEREOF

(76) Inventor: Jean-Paul Perraudin, Brussels (BE)

( * ) Notice: Subject to any disclaimer, the term of this patent is extended or adjusted under 35 U.S.C. 154(b) by 931 days.

This patent is subject to a terminal disclaimer.

(21) Appl. No.: 13/567,899

(22) Filed: Aug. 6, 2012

(65) Prior Publication Data

US 2013/0064809 A1    Mar. 14, 2013

Related U.S. Application Data

(63) Continuation of application No. 12/310,692, filed as application No. PCT/EP2007/056662 on Jul. 3, 2007, now Pat. No. 8,263,138.

(30) Foreign Application Priority Data

Jul. 3, 2006 (EP) .................. PCT/EP2006/006452

(51) Int. Cl.

| | | |
|---|---|---|
| *A61K 38/40* | (2006.01) | |
| *A61K 33/00* | (2006.01) | |
| *A61K 38/18* | (2006.01) | |
| *A61K 38/47* | (2006.01) | |
| *A61K 39/395* | (2006.01) | |
| *A61K 45/06* | (2006.01) | |
| *A01N 59/00* | (2006.01) | |
| *A01N 59/12* | (2006.01) | |

(52) U.S. Cl.
CPC ............... *A61K 38/40* (2013.01); *A01N 59/00* (2013.01); *A01N 59/12* (2013.01); *A61K 33/00* (2013.01); *A61K 38/18* (2013.01); *A61K 38/47* (2013.01); *A61K 39/395* (2013.01); *A61K 45/06* (2013.01)

(58) Field of Classification Search
None
See application file for complete search history.

(56) References Cited

U.S. PATENT DOCUMENTS

| 7,275,640 | B2 * | 10/2007 | Bourne et al. ............ 206/219 |
| 8,263,138 | B2 * | 9/2012 | Perraudin .................... 424/661 |
| 2003/0232021 | A1 * | 12/2003 | Schechter .................... 424/49 |
| 2005/0082512 | A1 | 4/2005 | Casez | |
| 2007/0116698 | A1 | 5/2007 | Perraudin | |
| 2009/0317378 | A1 | 12/2009 | Perraudin | |

FOREIGN PATENT DOCUMENTS

| EP | 1 068 871 A1 | 1/2001 |
| EP | 1068871 A1 * | 1/2001 |
| EP | 1 334 710 A1 | 8/2003 |
| WO | 97/26908 A1 | 7/1997 |
| WO | WO 01/03727 A1 | 1/2001 |
| WO | WO 02/097076 A1 | 12/2002 |

OTHER PUBLICATIONS

Kirstila et al, 1998 Journal of Dental Research 77(1): 73-80.*
Loimaranta et al, 1998 Oral Microbiology and Immunology 13: 378-381.*
Jacks et al, 1991 Biochem. Biophys. Research Commun. 178(3): 1202-1204.*
M. Lenander-Lumikari et al., "Lysozyme Enhances the Inhibitory Effects of the Peroxidase System on Glucose Metabolism of *Streptococcus mutans*," *Journal of Dental Research*; pp. 484-490; vol. 71, No. 3, Mar. 1992.
Jacks et al., 1991, Biochem. Biophys. Research Commun. 178(3): 1202-1204.
Jalil et al., "The Relationship Between 48-h Dental Plaque Accumulation in Young Human Adults and the Concentrations of Hypothiocyanite, 'Free' and 'Total' Lysozyme, Lactoferrin and Secretory Immunoglobulin A in Saliva," Archs Oral Biol., vol. 37, No. 1, pp. 23-28, 1992.
Soukka et al., "Combined Inhibitory Effect of Lactoferrin and Lactoperoxidase System on the Viability of *Streptococcus Mutans*, Serotype c," Scand J Dent Res., vol. 99, No. 5, pp. 390-396, 1991.
Valimaa et al., "Salivary Defense Factors in Herpes Simplex Virus Infection," J Dent Res., vol. 81, No. 6, pp. 416-421, 2002.
Halliwell, "Phagocyte-Derived Reactive Species: Salvation or Suicide?," Trends Biochem Sci., vol. 31, No. 9, pp. 509-515, 2006.
Playford et al., "Colostrum and Milk-Derived Peptide Growth Factors for the Treatment of Gastrointestinal Disorders," Am J Clin Nutr., vol. 72, No. 1, pp. 5-14, 2000.
Adolfsson-Erici et al., "Triclosan, a Commonly Used Bactericide Found in Human Milk and in the Aquatic Environment in Sweden," Chemosphere, vol. 46, pp. 1485-1489, Mar. 2002.
Tunio et al., "Epidermal Growth Factor in Saliva and Gastric Juice: Response to Histamine," Gut, vol. 37, pp. 335-339, 1995.
Rona, "Clinical Applications: Bovine Colostrum As Immune System Modulator," Am J Natural Med, vol. 5, No. 2, pp. 19-24, 1998.
Aug. 27, 2007 International Search Report issued in International Application No. PCT/EP2007/056662.

* cited by examiner

*Primary Examiner* — David H Kruse
(74) *Attorney, Agent, or Firm* — Oliff PLC (57) ABSTRACT

A composition for prophylactic and/or therapeutic medicinal applications, or plant protection applications, in particular for the control of microorganisms, either planktonic or organized in biofilms. The composition includes at least one ion selected from hypohalite, at least one compound selected from lactoferrin, lactoferrin peptide, lysozyme, immunoglobulins or a combination thereof, optionally hypothiocyanite, and optionally at least one growth factor.

17 Claims, 1 Drawing Sheet

US 9,555,081 B2

ANTIMICROBIAL COMPOSITION AND USES THEREOF

This application is a continuation of U.S. application Ser. No. 12/310,692, filed Mar. 4, 2009, now U.S. Pat. No. 8,263,138 which is a National Phase of International Application No. PCT/EP2007/05662, filed Jul. 3, 2007, which in turn claims priority to International Application No. PCT/EP2006/006452, filed Jul. 3, 2006.

FIELD OF THE INVENTION

The present invention relates to antimicrobial compositions. The present invention also relates to the use of said compositions for prophylactic and/or therapeutic medicinal or plant protection applications, in particular for the control of microorganisms, either planktonic or organized in biofilms adherent to the cell surfaces.

BACKGROUND OF THE INVENTION

The development of effective prophylactic and therapeutic agents for controlling microorganism either planktonic or organized in biofilms adherent to cell surfaces has proven problematic.

Prophylactic and therapeutic formulations and methods developed for the prevention of infections by control of the ecological microbial balance, in general, have only been partially successful.

In nutrient-limited ecosystems, such as the aquatic environment, bacteria have a marked tendency to attach to surfaces and initiate the formation of a biofilm. The biofilm is a collection of microcolonies with water channels in between and an assortment of cells and extra cellular polymers (glycoproteins, polysaccharides and proteins). These biofilms are also a severe problem in medical science, such as in oral health where they can cause dental plaque and periodontitis.

It is well known that natural antimicrobial agents are contained in most natural external mammalian secretions. In particular, the naturally occurring antimicrobial thiocyanate/peroxidase/$H_2O_2$ systems, lactoferrin, lactoferrin peptides, lysozyme and immunoglobulins present in secretion liquids have been extensively studied.

Antimicrobial thiocyanate/peroxidase/$H_2O_2$ systems imitate the effect of the peroxidases (sialoperoxidase and myeloperoxidase) which catalyze the transformation of halide or pseudo-halide into hypohalide or pseudo hypohalite in the presence of the hydrogen peroxide produced by some bacterial strains.

Lactoferrin is bacteriostatic by fixing ferric iron and making it unavailable for bacteria metabolism. However, when the microorganisms are organized in biofilm and that the biofilm can be protected by other biofilm layers, the lactoferrin has no or not sufficient antibacterial effect against the lower layer.

Lysozyme hydrolyses proteoglycans in the bacterial cell walls causing cell lysis. When the microorganisms are organized in biofilms and are hidden by several layers of biofilms, lysozyme alone or in combination with other antimicrobial agents such as lactoferrin has no effect against these microorganisms.

Immunoglobulins are able to react specifically against the microorganisms individually. The presence of several layers of biofilms and the characteristics of the biofilms avoid the action of the immunoglobulins alone or in combination with other antimicrobial agents such as lactoferrin to react against the individual microorganisms.

The ability of the antimicrobial agents contained in saliva to react significantly on the bacteria organized in biofilms depends largely on the thickness of the biofilm. In many cases, in the presence of several layers of biofilms, the upper layer protects the lower layer against the action of the naturally occurring antimicrobial agents described above. This lower layer contains $H_2O_2$ producers and will thus be responsible for the damage of the tissue composed of epithelial and fibroblast cells.

Some of these antimicrobial agents are able to bind the bacteria thereby avoiding the adhesion process on the mucosa! cells. However, these antimicrobial agents are not able to remove the biofilm.

The biofilm phenotype of some species has been shown to differ radically from the planktonic phenotype of the same organism. One of the facets in which biofilm bacteria differ the most profoundly from their planktonic counterparts, is in the critical matter of resistance to antibacterial agents. Results of in vitro studies showed *Staphylococcus epidermis* and *Staphylococcus aureus* were significantly more sensitive to the Lactoperoxidase system where the microorganisms are under planktonic cells than the biofilm cells, since the number of viable planktonic cells decrease by approximately 6 log units compared to a reduction of 1 log units or less in the number of biofilm cells.

The test results on the total bacteria count confirm that biofilm cells are more resistant than planktonic cells. This is believed to be due to a physical protection by the biofilm matrix or by an altered physiology of bacterial mode of growth.

In many cases, the bottom layer of biofilm will consist of anaerobic bacteria. As a result these biofilm cells may escape the inhibitory effect of the lactoperoxidase system, even though, under aerobic conditions, these cells have limited resistance to the lactoperoxidase system. These biofilm cells also escape the inhibitory effect of the lactoferrin, lysozyme and/or immunoglobulins.

Secretion liquids have long been known to be active against a number of bacteria, viruses, yeast and protozoa. But, saliva supplementation with thiocyanate/peroxidase/$H_2O_2$ systems has been shown to be ineffective in vivo on the salivary bacterial count. Formulation containing a combination of growth factor and saliva antibacterials has been described for use against biofilms adherent to cell surface. For instance, WO 01/03727 describes the use of a composition comprising a combination of a growth factor and at least one compound selected from peroxidase, lactoferrin, lactoferrin peptides, lysozyme and immunoglobulins for the prophylaxis and therapy of infectious diseases caused by microorganisms present in biofilms.

However, there still remains a need for improved compositions useful for the prophylaxis and/or therapy of diseases caused by microorganisms and in particular for the control of biofilms, thereby limiting the occurrence and progression of infectious diseases. It is the main object of the present invention to provide a composition effective for the prophylaxis and/or therapy of diseases caused by microorganisms and in particular it is another object of the present invention to provide a composition effective against planktonic microorganism and microorganism organized in biofilms, i.e. which compositions are able to disinfect surfaces.

SUMMARY OF THE INVENTION

The present invention therefore provides a composition comprising:

at least one ion selected from hypohalite,
at least one compound selected from lactoferrin, lactoferrin peptide, lysozyme, immunoglobulins or a combination thereof,
optionally hypothiocyanite, and
optionally at least one growth factor.

In an embodiment, said composition comprises at least one hypohalite ion, and hypothiocyanite, at least one compound selected from lactoferrin, lactoferrin peptide, lysozyme, immunoglobulins or a combination thereof, and optionally at least one growth factor.

The invention also provides a composition comprising:
at least one ion selected from hypohalite, hypothiocyanite or a combination thereof,
at least one compound selected from lactoferrin, lactoferrin peptide, lysozyme, immunoglobulins or a combination thereof, and
at least one growth factor.

The present invention also provides a composition comprising:
at least one ion selected from hypohalite, hypothiocyanite or a combination thereof, and
at least one compound selected from lactoferrin, lactoferrin peptide, lysozyme, immunoglobulins or a combination thereof.

The present invention also provides a pharmaceutical or plant protection composition comprising a composition according to the invention, and a pharmaceutically or a plant protection acceptable carrier.

The present invention further encompasses the use of a composition according to the invention as a medicament. In particular, the invention relates to the use of a composition according to the invention for the preparation of a medicament for the prophylaxis and/or therapy of diseases caused by microorganisms. In particular, the invention relates to the use of a composition according to the invention for the manufacture of a medicament for preventing, inhibiting or killing microorganisms either planktonic or organized as biofilms. Preferably said microorganisms are selected from bacteria, viruses, protozoas, yeast, fungi, parasites and the like.

The present invention also provides a method for the prophylaxis and/or therapy of diseases caused by microorganisms comprising administering to an individual in need thereof a composition according to the invention.

The present invention further encompasses the use of a composition for the manufacture of a medicament for preventing or treating diseases selected from gastro-intestinal infections, calculus and occurrence of caries, gingivitis, mucositis, periodontal diseases, vaginal diseases, herpes, acne, ulcers (*H. pylori*), tourista, cystitis, molluscum contagiosum or chlamydia infections. Therefore, the invention also provides methods for preventing or treating diseases selected from gastro-intestinal infections, calculus and occurrence of caries, gingivitis, mucositis, periodontal diseases, vaginal diseases, herpes, acne, ulcers, tourista, cystitis, molluscum contagiosum or chlamydia infections, comprising the step of administering to an individual in need thereof a composition according to the invention. Furthermore, the invention provides methods for prophylaxis and therapy of infectious diseases caused by microorganisms present in biofilms adherent to cell surfaces comprising the step of administering to an individual in need thereof a composition according to the invention.

It was surprisingly shown by the present inventor that an unexpected synergistic effect was obtained by the combination of hypohalite and/or hypothiocyanite with other antimicrobial agents such as lactoferrins, lysozyme or immunoglobulins together with growth factors or without growth factors.

It was surprisingly found that in association with hypohalite and/or hypothiocyanite, different growth factors in combination with antimicrobial agents are able to stimulate the growth of the fibroblast and/or epithelial cells and so to reactivate the activity of these cells destroyed by the binding of the pathogenic microorganisms organized in biofilms. This reactivation of the activity of fibroblast cells allows also the activation the epithelial cells which can be able by this action, to remove the microorganism biofilms from their cell surfaces. This removing of the microorganism biofilms yields them more accessible to the antibacterial, antiviral and candidacidal actions of the composition according to the invention.

The present invention also provides prophylactic and therapeutic methods for controlling, preventing or treating infections in caused by microorganisms, preferably present in biofilms adherent on cell surfaces, by the administration of prophylactic and therapeutic effective amounts of hypohalite and/or hypothiocyanite, together with effective amounts of lactoferrin, lactoferrin peptides, lysozymes and immunoglobulins (used alone and/or combined) and optionally effective amounts of growth factors (used alone and/or combined) as defined above to individuals in need thereof.

As used herein, the term "prophylactic" refers variously to compositions, medicaments, amounts or quantities, methods, uses and effects, etc., that prevent and/or aid in preventing infections caused by the presence of microorganisms, preferably organized in biofilms adhered to cell surfaces. As used herein, the term "therapeutic" refers variously to compositions, medicaments, amounts or quantities, methods, uses and effects, etc., that ameliorate infections caused by the presence of microorganisms, preferably organized in biofilms adhered to cell surfaces.

The present invention also relates to the use of a composition according to the invention for the control of plant-pathogenic organisms, preferably fungi and bacteria.

The present invention also relates to the use of a composition according to the invention for controlling plant-pathogenic bacteria and/or fungi on plants, and parts or locus thereof, in particular harvestable parts such as flowers, bulbs, tubers, fruits and the like.

The present invention also provides a method for controlling plant-pathogenic bacteria and/or fungi on plants, and parts or locus thereof, comprising the step of applying to the plant, or part or locus thereof a composition according to the present invention.

These and other objects of the invention will become apparent from the following specification.

DETAILED DESCRIPTION OF THE INVENTION

The compositions of the present invention include at least one ion selected from hypohalite together with at least one compound selected from lactoferrin, lactoferrin peptides, lysozyme and immunoglobulins and optionally hypothiocyanite and optionally at least a protein binding, by a means of a specific receptor, the epithelial and/or fibroblast cells and promoting growth of said cells such as for instance platelet derived growth factor (PDGF), fibroblast growth factor (FGF), transforming growth factor (TGF), angiogenin and epidermal growth factor (EGF).

For example, said composition may comprises (i) at least one hypohalite, (ii) at least one compound selected from lactoferrin, lactoferrin peptides, lysozyme and immunoglobulins, (iii) hypothiocyanite and (iv) optionally at least a protein binding, by a means of a specific receptor, the epithelial and/or fibroblast cells and promoting growth of said cells such as for instance platelet derived growth factor (PDGF), fibroblast growth factor (FGF), transforming growth factor (TGF), angiogenin and epidermal growth factor (EGF).

For example, said composition may comprises (i) at least one hypohalite, (ii) at least one compound selected from lactoferrin, lactoferrin peptides, lysozyme and immunoglobulins, and (iii) optionally at least a protein binding, by a means of a specific receptor, the epithelial and/or fibroblast cells and promoting growth of said cells such as for instance platelet derived growth factor (PDGF), fibroblast growth factor (FGF), transforming growth factor (TGF), angiogenin and epidermal growth factor (EGF), with the proviso that said composition does not comprise hypothiocyanite.

In an embodiment, the compositions of the present invention include (a) at least one ion selected from hypohalite and/or hypothiocyanite together with (b) at least one compound selected from lactoferrin, lactoferrin peptides, lysozyme and immunoglobulins on the one side and optionally (c) at least a protein binding, by a means of a specific receptor, the epithelial and/or fibroblast cells and promoting growth of said cells such as for instance platelet derived growth factor (PDGF), fibroblast growth factor (FGF), transforming growth factor (TGF), angiogenin and epidermal growth factor (EGF) on the other side.

Preferably said hypohalite is selected from hypochlorite, hypoiodite, hypobromite ions or a combination thereof.

In an embodiment, said composition is in a fluid such as liquid state and comprises at least one ion selected from hypochlorite, hypoiodite, hypobromite, at least one compound selected from lactoferrin, lactoferrin peptides, lysozyme, immunoglobulins or a combination thereof and optionally at least one growth factor selected from platelet derived growth factor, fibroblast growth factor, transforming growth factor, angiogenin, epidermal growth factor or a combination thereof. In a particular embodiment, said composition comprises at least one growth factor.

In an embodiment, said composition is in a fluid such as liquid state and comprises at least one ion selected from hypochlorite, hypoiodite, hypobromite, at least one compound selected from lactoferrin, lactoferrin peptides, lysozyme, immunoglobulins or a combination thereof, hypothiocyanite and optionally at least one growth factor selected from platelet derived growth factor, fibroblast growth factor, transforming growth factor, angiogenin, epidermal growth factor or a combination thereof. In a particular embodiment, said composition comprises at least one growth factor.

In an embodiment, said composition is in a fluid such as liquid state and comprises (a) at least one ion selected from hypochlorite, hypoiodite, hypobromite or hypothiocyanite or a combination thereof together with (b) at least one compound selected from lactoferrin, lactoferrin peptides, lysozyme, immunoglobulins or a combination thereof and (c) at least one growth factor selected from platelet derived growth factor, fibroblast growth factor, transforming growth factor, angiogenin, epidermal growth factor or a combination thereof.

In another embodiment, said composition is in a fluid such as liquid state and comprises (a) at least one ion selected from hypochlorite, hypoiodite, hypobromite or hypothiocyanite or a combination thereof together with (b) at least one compound selected from lactoferrin, lactoferrin peptides, lysozyme, immunoglobulins or a combination thereof.

Preferably said hypohalite ion is provided in a concentration ranging from 0.1 µM to 5000 µM, for example from 1 µM to 1000 µM, from 5 µM to 900 µM, from 5 µM to 800 µM, from 5 µM to 700 µM, from 5 µM to 600 µM, from 5 µM to 550 µM, from 10 µM to 550 µM, from 20 µM to 550 µM, from 30 µM to 550 µM, from 40 µM to 550 µM. Preferably said hypothiocyanite ion is provided in a concentration ranging from 0.1 µM to 5000 µM, for example from 1 µM to 1000 µM, from 5 µM to 900 µM, from 5 µM to 800 µM, from 5 µM to 700 µM, from 5 µM to 600 µM, from 5 µM to 550 from 10 µM to 550 µM, from 20 µM to 550 µM, from 30 µM to 550 µM, from 40 µM to 550 µM.

The hypohalite and/or hypothiocyanite are used isolated and can be produced chemically. They can also be isolated from their producing enzymatic system using different process such as removing the enzyme from the producing solution, using an immobilization system, precipitating the enzymatic system or by using ultrafiltration membranes. The hypohalite and/or hypothiocyanite are preferably produced using an enzymatic process by reacting at least an enzyme of the peroxidase type with an oxidizable substrate and an oxygen donor, according to which i) an aqueous reaction mix is prepared comprising in addition to the oxidizable substrate and the oxygen donor, the enzyme in solid and divided phase, ii) aqueous reaction mix is fractioned in a fraction enriched with the enzyme in solid and divided phase, and a fraction free of said enzyme containing said hypohalite and/or hypothiocyanite ions.

A suitable production process is described in WO 02/097076, which recitations relating to the production process are hereby incorporated herein as part hereof. Said process comprises the steps of bringing into contact at least: one enzyme of the peroxidase type, and one oxidizable substrate, an oxygen donor, according to which: a) an aqueous reaction bath is formed, which bath comprises, in addition to the oxidizable substrate and the oxygen donor, said peroxidase in the solid and divided phase, but in the free state, b) the aqueous reaction bath is separated into a fraction which is enriched in enzyme in solid and divided phase and into a fraction which lacks said enzyme and from which the hypohalite and/or hypothiocyanite is obtained. The process can have the following variants: The oxidizable substrate, possibly in aqueous phase, is introduced into the aqueous reaction bath. The enzyme, in the state of a solid and divided phase or in liquid phase, is introduced into the reaction bath. The enzyme is discharged from the reaction bath. The process can be performed continuously or discontinuously. Aggregates may be used which are formed of solid particles inert with respect to the enzyme, said aggregates comprising or incorporating, in a free state, said enzyme, said aggregates being distributed in the aqueous reaction mix. Said aggregates may be flakes, obtained by introducing into the reaction mix, a flocculating agent. The flocculating agents which can be used are selected from the group comprising anion or cation polymeric flocculating agents, such as polysaccharides, heteropolysaccharides or polyacrylamines. Flocculating agents can be added in the reaction mix, in proportions varying from $0.1 \cdot 10^{-6}$ to 10 g/l of reaction mix. Said aggregates may be coagulation products obtained by introducing into the reaction mix a coagulating agent. In an embodiment, a thickening agent may be introduced into the reaction mix. Coagulating agents can be chosen for example among iron or aluminum salts, such as for example: sulfate aluminum, chloride aluminum, sodium aluminate, aluminum polyhydroxychlorure, aluminum polyhydroxysulfate, polyhydroxychlorosulfate of aluminum, aluminum polychlorosulfate basic, aluminum polyhydroxychlorosilicate, aluminum fluorosulfate, sulfates ferrous, ferric sulfate, ferric chloride, chlorosulfate ferric, soda, or of the chloride homopolymers dimethyl diallyl ammonium. Coagulating agents can be added in the reaction mix, in proportions varying from $0.1 \cdot 10^{-6}$ to 10 g/l of reaction medium. The enzyme in solid phase can also be in the form of an emulsion in the reaction mix, into which an emulsifying agent can be added. As used herein "emulsion" refers to any suspension containing a non-immobilized enzyme, likely to be obtained by addition of emulsifiers such as for example fatty substances or soya lecithin or hydrocarbons. The enzyme can also be comprised in a microorganism expressing said enzyme.

As used herein the term "aggregate" refers to any formulation allowing to maintain in a solid and divided phase but in a free state in the reaction mix the enzyme by addition of coagulating, flocculating, emulsifying agent in presence or not of a thickening agent, which allowing the isolation and the recycling of said enzyme from the reaction mix at the end of the reaction. The formation of the aggregates can be carried out by successive addition of a coagulating agent and of a flocculating agent. Optionally organics or mineral thickening agent, chemically compatible with the aggregates can be added with the mixture. This thickening agent can be introduced into the mix simultaneously with the introduction of the enzyme or after formation of the aqueous reaction mix. This thickening agent can be selected among clays, kaolin, silica, silicates, or any other compatible mineral agent. The thickening agent can be added in the reaction medium, in proportions varying of 0.1 to 100 g/l of reaction medium.

As used herein "free state" refers to a state wherein said enzyme is comprised in said aggregate without formation of ionic or covalent bond between said enzyme and the aggregating agent.

The pH of the reaction mix containing the enzyme, can be stabilized or corrected by addition of a pH correcting agent, which will be selected among mineral or organic acids or bases.

The hypohalite and/or hypothiocyanite can be produced in a reactor comprising a compartmentalized tank which can be partly or totally closed, and which can be made of metal or of synthetic material, said tank comprising a loading orifice, overflows and/or siphoid partitions, allowing the passage from one compartment to another.

The reactor may comprise three or four compartments, two or three of which are subjected to permanent stirring: the first compartment is intended to receive the enzyme, optionally the coagulating and the thickening agent, it is subjected to an agitation at fast speed, the second optionally receives the flocculating agent and optionally a pH corrector, and is under gentle stirring, the oxidation reaction is performed in the third compartment, wherein the oxidizable substrate as well as oxygen donor are added under gentle stirring. In the fourth compartment, the separation of the hypohalite and/or hypothiocyanite ions from the reaction mix is performed using a lamellar clarifier comprising a low feed, an overflow connected to the exit orifice, a low point of dynamic extraction of the settled solid matters.

Alternatively, the enzyme and the optional emulsifying agent are introduced into the first compartment, and the oxidation reaction is performed in the second compartment into which the oxidizable substrate is added. The third compartment is a recovery unit, which allows the uninterrupted pumping of the solution comprising hypohalite and/or hypothiocyanite ions and other residual substrates towards a separation unit, which can be a coalescor, a flotator, a centrifugal machine, a filter or a cyclone.

The oxidizable substrate useful for the preparation of the hypohalite and/or hypothiocyanite ions of the present invention can be chosen from a group consisting of negatively charged halogens, and their derivatives, and negatively charged pseudo-halogens, and their derivatives. As used herein the term "halogens" refers to elements that belong to Group VII of the Periodic Table of Elements, in their negatively-charged monovalent states, which includes bromide, chloride and iodide. The term "pseudo-halogens" refers to monovalent negatively charged ions selected from the group comprising thiocyanate ions, bisulfite ions, hydrosulfite ions, metabisulfite ions, and/or nitrite ions and the like. The oxidizable substrates suitable herein will be preferably selected according to the peroxidase used. Examples of suitable substrates include but are not limited to thiocyanate salts, such as sodium thiocyanate, potassium thiocyanate, ammonium thiocyanate, ferric thiocyanate, sodium bisulfite ($NaHSO_3$), sodium hydrosulfite ($Na_2S_2O_4$), sodium metabisulfite ($Na_2S_2O_5$), sodium nitrite ($NaNO_2$) or potassium nitrite ($KNO_2$), sodium hypochlorite (NaOCl) and potassium iodide (Kl) and mixtures thereof.

The immobilized peroxidases which can be used to produce the hypohalite and/or hypothiocyanite ions for use in the present invention, include plant (vegetable) peroxidases, such as horseradish peroxidase, and mammalian peroxidases, such as salivary peroxidases, lactoperoxidases, myeloperoxidases and eosinophil peroxidase. These peroxidases may be extracted (isolated) from natural material (for example, saliva, human and bovine milk) or produced by natural of chemical methods, all of which are well known to those skilled in the art. These peroxidases also include those peroxidases that are produced by recombinant DNA techniques, also well known in the art. Human and bovine lactoperoxidase may for instance be produced by microorganisms (for example transformed *Pichia* or transgenic animals such as transgenic cows) carrying a cDNA expressing said protein.

Depending on the hypohalite and/or hypothiocyanite to be produced, different enzymatic systems can be used. For example, salivary peroxidase can be used to produce hypothiocyanite, hypoiodite ions and/or mixtures thereof by using as oxidizable substrate thiocyanate, iodide and/or mixtures thereof in the presence of hydrogen peroxide. Lactoperoxidase can be used to produce hypothiocyanite, hypoiodite ions and/or mixtures thereof by using as oxidizable substrate thiocyanate, iodide and/or mixtures thereof in the presence of hydrogen peroxide. Myeloperoxidase can be used to produce hypothiocyanite, hypoiodite, hypochlorite ions and/or mixture thereof by using as oxidizable substrate thiocyanate, chloride, iodide ions and/or mixtures thereof, in the presence of hydrogen peroxide. Horseradish peroxidase can be used to produce hypoiodite, hypochlorite ions and/or mixture thereof by using as oxidizable substrate chlorides ions, iodides ions and/or mixtures thereof in the presence of hydrogen peroxide. Plant peroxidase can be used to produce hypothiocyanite, hypochlorite, hypobromite, hypoiodite ions and/or a mixture thereof by using as oxidizable substrate thiocyanates, chloride bromides iodide and/or mixture thereof in the presence of hydrogen peroxide. Non-limiting examples of suitable peroxidases and/or oxidoreductases include enzymes of vegetable origin such as for example horseradish peroxidase (E.C. n° 1.11.1.7) or soya peroxidase, nitrate oxidoreductase-NADPH (E.C. n° 1.6.6.1) of cereals, enzymes from fungi such as for example glucose oxidase (E.C. n° 1.1.3.4), catalase (E.C. n° 1.11.1.6), beta-galactosidase (E.C. n° 3.2.1.23) and nitrate oxydoreductase-NADPH (E.C. n° 1.6.6.2) of *Aspergillus*, enzymes of bacterial origin such as for example NADH-Peroxidase (E.C. n° 11.1.1) of *Enterococcus*, NADPH oxidoreductase (E.C. n° 1.6.99.3) of *Vibrio*, nitrate reductase (E.C. n° 1.9.6.1) of *Colibacilli*, oxidase lactique dismutase (E.C. n° 1.1.3.2) of *Pediococcus*, superoxide dismutase (E C n° 1.15.1.1) of *Colibacilli*, *Arthromyces* peroxidase (E C n° 1.11.1.1), the beta-galactosidase (E C n° 3.2.1.23) of *Colibacilli*, enzymes of animal origin such as for example xanthineoxidase (E.C. n° 1.1.3.22) of milk, lactoperoxidase (E.C. n° 1.11.1.7) of milk, the leucocytic myeloperoxidase (E.C. n° 1.11.1.7), nitric oxide synthase (E.C. n° 1.14.13.39) of nervous tissues, the superoxide dismutase (E.C. n° 1.15.1.1) of erythrocytes, sulfite oxidase (E.C. n° 1.8.3.1) of hepatocytes.

The enzymes can be added in the reaction medium, in proportions varying from 0.02 to 10 g/l of reaction medium.

The oxidizable substrates can be added in the reaction medium, in proportions varying from 0.05 mM to 15 mM per liter of reaction medium, The oxygen donor according to the present invention can be hydrogen peroxide and any inorganic peroxide such as metal peroxides, for example the peroxide of magnesium or of sodium or organic peroxides such as benzyl peroxides or the urea peroxide, but also the peracetic acid, the potassium permanganate and percarbonates. Generally, any chemical compound likely to produce hydrogen peroxide can be used. Advantageously the oxygen donors are added in the reaction medium, in proportions varying from 0.05 mM to 15 mM per liter of reaction medium. Said oxygen donor can be in the form of a complementary enzymatic system which produces oxygen peroxide, which comprises an oxidizable substrate and an enzyme for example of the oxidoreductase type, specific of this substrate.

Non-limiting examples of enzymatic systems suitable for the production of the oxygen donor include glucose oxidase/glucose, galactose oxidase/galactose, urate oxidase/u rate, choline oxidase/choline, glycine oxidase/glycine, glycollate oxidase/glycollate, L-sorbose oxidase/L-sorbose, amine oxidase/primary amine, glutamate oxidase/glutamate, alcohol oxidase/alcohol, NAD(P)H oxidase/NAD(P)H, superoxide dismutase/oxygen free radical.

The above-mentioned enzymatic systems are able in the presence of oxygen and water to produce hydrogen peroxide which will be used as oxygen donor in the enzymatic system in the process for producing hypohalite and/or hypothiocyanite. Alternatively, the oxygen donor can be selected among hydrogen peroxide-producing-microorganisms such as *Streptococcus* and/or *Lactobacillus*.

As utilized herein, the term "mM" (millimole) identifies that quantity in grams corresponding to the molecular weight of the composition divided by one thousand.

In an embodiment, the present invention provides a composition comprising:
  a lactoferrin,
  at least one ion selected from hypochlorite, hypobromite, hypoiodite, hypothiocyanite or a combination thereof, and
  optionally at least one growth factor preferably selected from platelet derived growth factor, fibroblast growth factor, transforming growth factor, angiogenin, epidermal growth factor or a combination thereof. In a preferred embodiment, the composition comprises additionally at least one growth factor selected from platelet derived growth factor, fibroblast growth factor, transforming growth factor, angiogenin, epidermal growth factor or a combination thereof. In a preferred embodiment, said composition comprises at least one ion selected from hypochlorite, hypobromite, hypoiodite. In another preferred embodiment, said composition comprises at least two ions: hypothiocyanite and one ion selected from hypochlorite, hypobromite, hypoiodite.

In the compositions according to the present invention, lactoferrin, presented under different iron saturated forms from 0% of iron (apo-lactoferrin) to 100% of iron saturation (Iron saturated lactoferrin) can be provided from different sources including mammalian sources for instance bovine lactoferrin from bovine secretions liquids for example bovine milk, human lactoferrin from human secretion liquids for example human milk, cDNA human like-lactoferrin or bovine like-lactoferrin produced by microorganisms for example *Pichia* or from transgenic animals for example transgenic cows, all known in the art. In an embodiment, lactoferrin is provided in a concentration ranging from 0.1 µg to 5000 mg/l of composition or from 0.1 µg to 5000 mg/kg of composition. Preferred dosages ranges of lactoferrin are from 0.001 g to 10 g, preferably from 0.01 g to 0.1 g per kg bodyweight per day or per 100 ml of liquid, gel, paste or other formulation.

In an embodiment, the present invention provides a composition comprising:
  lactoferrin peptides,
  at least one ion selected from hypochlorite, hypobromite, hypoiodite, hypothiocyanite or a combination thereof, and
  optionally at least one growth factor preferably selected from platelet derived growth factor, fibroblast growth factor, transforming growth factor, angiogenin, epidermal growth factor or a combination thereof. In a preferred embodiment, the composition comprises additionally at least one growth factor selected from platelet derived growth factor, fibroblast growth factor, transforming growth factor, angiogenin, epidermal growth factor or a combination thereof. In a preferred embodiment, said composition comprises at least one ion selected from hypochlorite, hypobromite, hypoiodite. In another preferred embodiment, said composition comprises at least two ions: hypothiocyanite and one ion selected from hypochlorite, hypobromite, hypoiodite.

Lactoferrin peptides are peptides produced by the action of a protease or a combination of proteases on lactoferrin. The proteases can be pepsin, chymotrypsin or any of all other proteases (proteolytic enzymes) used alone or in combined to proteolyse lactoferrin from any source such as described hereabove. For example said lactoferrin peptide is lactoferricin. Lactoferricin is a lactoferrin-derived peptide generated by acid-pepsin hydrolysis. Suitable lactoferrin peptides are described in Lactoferrin: Structure, Function and Applications. 2000. Elsevier, K. Simazaki et al. Editors, pages 164-171, on pages 239-243, and on pages 273-277, and in Advances in Lactoferrin Research, Edited by Spik et al. Plenum Press, 1998, on page 285-291, incorporated herein by reference.

In an embodiment, lactoferrin peptide is provided in a concentration ranging from 0.1 µg to 5000 mg/l of composition or from 0.1 µg to 5000 mg/kg of composition. Useful concentration can be from 10 µg to 10 g of lactoferrin peptides per liter but preferably 100 µg to 100 mg of lactoferrin peptides per liter per kg bodyweight per day or per 100 ml of liquid, gel, paste or other formulation.

In an embodiment, the present invention provides a composition comprising:
lysozyme,
at least one ion selected from hypochlorite, hypobromite, hypoiodite, hypothiocyanite or a combination thereof, and
optionally at least one growth factor preferably selected from platelet derived growth factor, fibroblast growth factor, transforming growth factor, angiogenin, epidermal growth factor or a combination thereof. In a preferred embodiment, the composition comprises additionally at least one growth factor selected from platelet derived growth factor, fibroblast growth factor, transforming growth factor, angiogenin, epidermal growth factor or a combination thereof. In a preferred embodiment, said composition comprises at least one ion selected from hypochlorite, hypobromite, hypoiodite. In another preferred embodiment, said composition comprises at least two ions: hypothiocyanite and one ion selected from hypochlorite, hypobromite, hypoiodite.

In these compositions, lysozyme can be provided from different sources including mammalian lysozyme for instance bovine lysozyme from bovine secretion liquids for example bovine milk, human lysozyme from human secretion liquids for example human milk, egg white lysozyme from egg white for example hen egg white, cDNA human like-lysozyme or bovine like-lysozyme produced by microorganisms for example *Pichia* or from transgenic animals for example transgenic cows. In an embodiment, lysozyme is provided in a concentration ranging from 0.1 µg to 5000 mg/l of composition or from 0.1 µg to 5000 mg/kg of composition. Preferred dosages ranges of lysozyme are from 0.001 g to 50 g, preferably from 0.01 g to 10 g, more preferably from 0.01 g to 0.1 g per kg bodyweight per day or per 100 ml of liquid, gel, paste or other formulation.

In an embodiment, the present invention provides a composition comprising:
immunoglobulins,
at least one ion selected from hypochlorite, hypobromite, hypoiodite, hypothiocyanite or a combination thereof, and
optionally at least one growth factor preferably selected from platelet derived growth factor, fibroblast growth factor, transforming growth factor, angiogenin, epidermal growth factor or a combination thereof. In a preferred embodiment, the composition comprises additionally at least one growth factor selected from platelet derived growth factor, fibroblast growth factor, transforming growth factor, angiogenin, epidermal growth factor or a combination thereof. In a preferred embodiment, said composition comprises at least one ion selected from hypochlorite, hypobromite, hypoiodite. In another preferred embodiment, said composition comprises at least two ions: hypothiocyanite and one ion selected from hypochlorite, hypobromite, hypoiodite.

In these compositions, immunoglobulins can be provided from different sources including mammalian immunoglobulins for instance bovine immunoglobulins from bovine secretions liquids for example blood, colostrum, milk and other derivates, human immunoglobulins from human secretion liquids for example blood, milk and other derivates, egg immunoglobulins from egg yolk. That undertakes also immunoglobulins produced from secretion liquids of immunized animals. Purified immunoglobulin preparations known in the art and commercially available may also be used. In an embodiment, immunoglobulin is provided in a concentration ranging from 0.1 µg to 100 g/l of composition or from 0.1 µg to 100 g/kg of composition. Preferred dosages ranges of immunoglobulins are from 0.001 g to 1000 g, preferably from 0.001 g to 100 g, more preferably from 0.01 g to 10 g, most preferably from 0.05 g to 1 g per kg bodyweight per day or per 100 ml of liquid, gel, paste or other formulations.

The use of different of these above-mentioned compounds together has a synergetic effect.

In these compositions, the growth factor component can be provided from any source known in the art. Preferred dosages ranges of growth factors are from 1 ppb to 100 mg, preferably from 0.001 mg to 100 mg, more preferably from 0.01 mg to 10 mg, most preferably from 0.1 mg to 1 g per kg bodyweight per day or per 100 ml of liquid, gel, paste or other formulations.

In an embodiment, the present invention provides a composition comprising:
at least one ion selected from hypochlorite, hypobromite, hypoiodite, hypothiocyanite or a combination thereof, and
at least one compound selected from lactoferrin, lactoferrin peptides, lysozymes, immunoglobulins or a combination thereof, and
platelet derived growth factor. In a preferred embodiment, said composition comprises at least one ion selected from hypochlorite, hypobromite, hypoiodite. In another preferred embodiment, said composition comprises at least two ions: hypothiocyanite and one ion selected from hypochlorite, hypobromite, hypoiodite.

In these compositions, the platelet derived growth factor can be provided from mammalian platelets for instance human or pig platelets or from mammalian secretion for instance bovine and human secretions liquids for example colostrum, milk and other derivates, manufactured by recombinant DNA technique, chemically synthesized, or a mixture thereof, all known in the art.

In an embodiment, the present invention provides a composition comprising:
at least one ion selected from hypochlorite, hypobromite, hypoiodite, hypothiocyanite or a combination thereof, and
at least one compound selected from lactoferrin, lactoferrin peptides, lysozymes, immunoglobulins or a combination thereof, and
fibroblast growth factor. In a preferred embodiment, said composition comprises at least one ion selected from hypochlorite, hypobromite, hypoiodite. In another preferred embodiment, said composition comprises at least two ions: hypothiocyanite and one ion selected from hypochlorite, hypobromite, hypoiodite.

In these compositions, the fibroblast growth factor can be provided from hypophyse, brain, hypothalamus, retin surrenal gland, and kidney. He can also provide from mammalian secretions for instance bovine and human secretions liquids for example colostrum, milk and other derivates, manufactured by recombinant DNA techniques, chemically synthesized, or a mixture thereof, all known in the art.

In an embodiment, the present invention provides a composition comprising:
- at least one ion selected from hypochlorite, hypobromite, hypoiodite, hypothiocyanite or a combination thereof, and
- at least one compound selected from lactoferrin, lactoferrin peptides, lysozymes, immunoglobulins or a combination thereof, and
- transforming growth factor. In a preferred embodiment, said composition comprises at least one ion selected from hypochlorite, hypobromite, hypoiodite. In another preferred embodiment, said composition comprises at least two ions: hypothiocyanite and one ion selected from hypochlorite, hypobromite, hypoiodite.

In these compositions, the transforming growth factor can be provided from mammalian blood platelet, for instance pig blood platelet, from mammalian secretions for instance from bovine and human secretions liquids for example colostrum, milk and other derivates, manufactured by recombinant DNA techniques, chemically synthesized, or a mixture thereof, all known in the art.

In an embodiment, the present invention provides a composition comprising:
- at least one ion selected from hypochlorite, hypobromite, hypoiodite, hypothiocyanite or a combination thereof, and
- at least one compound selected from lactoferrin, lactoferrin peptides, lysozymes, immunoglobulins or a combination thereof, and
- epidermal growth factor. In a preferred embodiment, said composition comprises at least one ion selected from hypochlorite, hypobromite, hypoiodite. In another preferred embodiment, said composition comprises at least two ions: hypothiocyanite and one ion selected from hypochlorite, hypobromite, hypoiodite.

In these compositions, the epidermal growth factor can be provided from different tissues and biological liquids of mammalian species, from bovine and human secretions liquids for example colostrum, milk and other derivates, manufactured by recombinant DNA techniques, chemically synthesized, or a mixture thereof, all known in the art.

In an embodiment, the present invention provides a composition comprising:
- at least one ion selected from hypochlorite, hypobromite, hypoiodite, hypothiocyanite or a combination thereof, and
- at least one compound selected from lactoferrin, lactoferrin peptides, lysozymes, immunoglobulins or a combination thereof, and
- angiogenin. In a preferred embodiment, said composition comprises at least one ion selected from hypochlorite, hypobromite, hypoiodite. In another preferred embodiment, said composition comprises at least two ions: hypothiocyanite and one ion selected from hypochlorite, hypobromite, hypoiodite.

In these compositions, the angiogenin growth factor can be provided from different tissues and biological liquids of mammalian species, from bovine and human secretions liquids for example colostrum, milk and other derivates, manufactured by recombinant DNA techniques, chemically synthesized, or a mixture thereof, all known in the art.

In an embodiment, the present invention provides a composition comprising colostrum and/or whey colostrum for providing a source of said at least one growth factors. Preferably, the present invention provides a composition comprising: (a) —at least one ion selected from hypochlorite, hypobromite, hypoiodite, hypothiocyanite or a combination thereof, and (b) at least one first compound selected from lactoferrin, lactoferrin peptides, lysozymes, immunoglobulins or a combination thereof, and (c) at least one second compound selected from colostrum, whey colostrum, platelet derived growth factor, fibroblast growth factor, transforming growth factor, angiogenin, epidermal growth factor or a combination thereof. In a preferred embodiment, said composition comprises at least one ion selected from hypochlorite, hypobromite, hypoiodite. In another preferred embodiment, said composition comprises at least two ions: hypothiocyanite and one ion selected from hypochlorite, hypobromite, hypoiodite.

In an embodiment, the present invention provides a composition comprising a hypohalite and/or hypothiocyanite and a lactoferrin or lactoferrin peptide and colostrum and/or whey colostrum. In a preferred embodiment, said composition comprises at least one hypohalite ion selected from hypochlorite, hypobromite, hypoiodite. In another preferred embodiment, said composition comprises at least two ions: hypothiocyanite and one ion selected from hypochlorite, hypobromite, hypoiodite.

In an embodiment, the present invention provides a composition comprising a hypohalite and/or hypothiocyanite and a lysozyme and colostrum and/or whey colostrum. In a preferred embodiment, said composition comprises at least one hypohalite ion selected from hypochlorite, hypobromite, hypoiodite. In another preferred embodiment, said composition comprises at least two ions: hypothiocyanite and one ion selected from hypochlorite, hypobromite, hypoiodite.

In an embodiment, the present invention provides a composition comprising a hypohalite and/or hypothiocyanite and an immunoglobulin and colostrum and/or whey colostrum. In a preferred embodiment, said composition comprise at least one hypohalite ion selected from hypochlorite, hypobromite, hypoiodite. In another preferred embodiment, said composition comprises at least two ions: hypothiocyanite and one ion selected from hypochlorite, hypobromite, hypoiodite.

The above mentioned compositions may further comprise a compound selected from triclosan, chlorhexidine, cetylpyridinium, or a combination thereof. Chlorhexidine can be chemically or naturally produced chlorhexidine Preferred concentrations of chlorhexidine for use herein are ranging from 0.1 µg to 100 g/l. Triclosan can be chemically or naturally produced. Preferred concentrations of triclosan for use herein are ranging from 0.1 µg to 100 g/l. Cetylpyridinium can be chemically or naturally produced. Preferred concentrations of Cetylpyridinium for use herein are ranging from 0.1 µg to 100 g/l.

In an embodiment, the present invention provides the present composition in a liquid form. In a preferred embodiment, the liquid composition according to the invention comprises a combination of at least three compounds: a first compound selected from the group comprising lactoferrin, lactoferrin peptide, lysozyme, immunoglobulins, or a combination thereof, a second compound selected from the growth factors and a third compound selected from the group of ions comprising $OSCN^-$ (hypothiocyanite), $OBr^-$ (hypobromite); $OI^-$ (hypoiodite) and $OCl^-$ (hypochlorite), or a combination thereof. Preferably, said third compound is selected from hypoiodite or hypochlorite, or a combination thereof. In another preferred embodiment, said third compound is hypothiocyanite and a forth compound is selected from hypochlorite or hypoiodite or a combination thereof.

In another embodiment, the liquid composition according to the invention comprises a combination of at least two compounds: a first compound selected from the group comprising lactoferrin, lactoferrin peptide, lysozyme, immunoglobulins, or a combination thereof, and a second compound selected from the group of ions comprising OSCN⁻ (hypothiocyanite), hypobromite, OI⁻ (hypoiodite) and OCl⁻ (hypochlorite), or a combination thereof. Preferably, said second compound is selected from hypoiodite or hypochlorite, or a combination thereof.

In another preferred embodiment, said second compound is hypothiocyanite and a third compound is selected from hypochlorite or hypoiodite or a combination thereof.

In the present invention, the hypohalite and/or hypothiocyanite used in the composition are isolated and not in combination with the peroxidase system which usually comprises the enzyme, the substrate and the oxygen donor. The hypohalite and/or hypothiocyanite ions when isolated have an activity which is different from the ion when in presence of the peroxidase system.

The pharmaceutical compositions in accordance with the invention can be prepared according to conventional pharmaceutical compounding techniques. See, for example, Remington's Pharmaceutical Sciences, 18th Ed. (1990, Mack Publishing Co., Easton, Pa.). Typically, a therapeutically effective amount of the active ingredient will be admixed with a pharmaceutically acceptable carrier. The carrier may take a wide variety of forms depending on the form of preparation desired for administration, e.g., intravenous, oral or parenteral. The compositions may farther contain antioxidizing agents, stabilizing agents, preservatives and the like.

As used herein, the term "pharmaceutically acceptable" carrier means a non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; malt, gelatine, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerine, sorbitol, mannitol and polyethylene glycol; esters such as ethyl oleate and ethyl laurate, agar; buffering agents such as magnesium hydroxide and aluminium hydroxide; alginic acid; pyrogen-free water; isotonic saline, Ringer's solution; ethyl alcohol and phosphate buffer solutions, as well as other non-toxic compatible substances used in pharmaceutical formulations.

Wetting agents, emulsifiers and lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Examples of pharmaceutically acceptable antioxidants include, but are not limited to, water soluble antioxidants such as ascorbic acid, cysteine hydrochloride, sodium bisulfite, sodium metabisulfite, sodium sulfite, and the like; oil soluble antioxidants, such as ascorbyl palmitate, butylated hydroxyanisole (BHA), butylated hydroxytoluene (BHT), lecithin, propyl gallate, aloha-tocopherol and the like; and the metal chelating agents such as citric acid, ethylenediamine tetraacetic acid (EDTA), sorbitol, tartaric acid, phosphoric acid and the like.

The compositions according to the present invention can be administered to an individual in a number of ways depending on the area to be treated. The term "individual" as used herein refers to an animal such as vertebrates. Examples of these vertebrates include fish, birds, and mammal. The individual will preferably be a human, but may also be a domestic livestock, poultry, fish, laboratory or pet animals. Administration may be vaginal, rectal, intranasal, oral, by inhalation, or parenteral, for example by intravenous drip, subcutaneous, intratumor, intraperitoneal, intralymphatic or intramuscular injection.

For oral administration, the composition for use in accordance with the invention can be formulated into liquid preparations such elixirs, solutions, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like.

For parenteral administration, the composition for use in accordance with the invention may be used with a pharmaceutical carrier and administered as either a solution or a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilising agents, buffers and the like.

A variety of administration routes are available. The particular mode selected will depend of course, upon the particular drug selected, the severity of the disease state being treated and the dosage required for therapeutic efficacy. The methods of this invention, generally speaking, may be practiced using any mode of administration that is medically acceptable, meaning any mode that produces effective levels of the active compounds without causing clinically unacceptable adverse effects. Such modes of administration include oral, rectal, sublingual, nasal, transdermal or parenteral routes. The term "parenteral" includes subcutaneous, intravenous, epidural, irrigation, intramuscular, release pumps, or infusion.

The composition for use herein may be formulated with a pharmaceutically-acceptable carrier in any other suitable manner desired for administration in the particular situation. For example, the compositions may be formulated as a liquid toothpaste, mouthwash, and spray for oral administration in the treatment of mouth infections. Alternatively, the compositions may be formulated in a topical formulation (such as a spray, gel, cream, eye drops, shampoo, etc.) and/or incorporated in a bandage or a pad for topical administration to the skin, eyes, hair, etc., of individuals in need thereof. Finally, the compositions may also be formulated as an injectable solution for internal application.

The different possible compositions according to the present invention may be prepared for prophylactic and/or therapeutic purposes, as desired and needed, for permitting the administration of prophylactic and/or therapeutic effective amounts of the individual components thereof to an individual in need thereof for preventing and/or treating infections.

The compositions according to the present invention may be used to prevent and/or treat infections in humans or animals.

The compositions according to the present invention are particularly suitable for the prophylaxis and/or therapy of diseases caused by microorganisms either planktonic or organized as biofilms.

As used herein the term "planktonic" refers to isolated free-floating microorganisms whose movements are controlled by water movement (not attached to surfaces).

As used herein the term "biofilm" refers to a slime-like matrix within which a consortium of microorganisms flourishes. These biofilms may either grow over surfaces, or occupy voids in a porous medium.

The present invention provides methods for the prophylaxis and/or therapy of diseases caused by microorganisms comprising administering to an individual in need thereof a composition according to the invention. In an embodiment, said method comprises administering to an individual in need thereof a composition comprising (a) at least one ion selected from hypohalite, hypothiocyanite or a combination thereof, (b) at least one compound selected from lactoferrin, lactoferrin peptide, lysozyme, immunoglobulins or a combination thereof, and optionally (c) at least one growth factor.

Said microorganisms can be bacteria, viruses, protozoas, yeast, fungi, parasites and the like. In an embodiment, said microorganism is responsible of gastro-intestinal infections. In an embodiment said gastro intestinal infection is causing diarrhea or intestinal ulcers. Preferably said microorganism responsible of gastro-intestinal infection is selected from the group comprising Shigella, Salmonella, E. coli, Vibreo colera, Pseudomonas (Ps. pyocyanea), Staphylococcus (Staph. albus, aureus), Streptococcus (Strep. viridans, Strep. faecalis, B-Streptococcus), Proteus, Helicobacter pylori and the like, preferably H. pylori.

In another embodiment, said microorganism is involved in the formation of calculus and occurrence of caries, gingivitis, mucositis and/or other periodontal diseases. In another embodiment, said microorganism is causing acne. In another embodiment, said microorganism is responsible of vaginal diseases. In another embodiment, said microorganism is responsible of molluscum contagiosum.

In a further embodiment, said microorganism is an enveloped virus. For example, said virus is causing herpes. Preferably said herpes is selected from herpes simplex paramyxoviruses (such as human parainfluenza viruses), the family of orthomyxoviruses (such as the influenza type viruses A and B), rotaviruses, coronaviruses, herpes viruses (such as Varicella-zoster virus, cytomegalovirus, Epstein-Barr virus and HHV6) or retroviruses (such as Human T-cell leukemia virus-1, bovine leukemia virus and simian immunodeficiency virus SW).

The composition according to the present invention can be used for the prophylaxis or therapy of infectious diseases caused by microorganisms forming biofilms on various types of human cell surfaces, such as for instance skin, ocular mucosa, ortho-rhino-laryngic spheres, gastro-enterologic cells and cell surfaces of the urogenital system.

The compositions according to the present invention are for instance useful for treating dental plaque, periodontal diseases, ulcers, tourista, bacterial vaginitis, vaginosis, cystitis, molluscum contagiosum, chlamydia infections.

The compositions according to the present invention, and for use in accordance to the present invention, may comprise, in addition to the afore-mentioned compounds, a pharmaceutically acceptable excipient, carrier, buffer, stabilizer or other materials well known to those skilled in the art. Such materials should be non-toxic and should not interfere with the efficacy of the active ingredients. The precise nature of the carrier or other material may depend on the route of administration. Those of relevant skill in the art are well able to prepare suitable solutions.

In a therapeutic context, i.e. where the biological effect of the compositions to an individual is beneficial, administration is preferably in a "therapeutically effective amount", this being sufficient to show benefit to the patient. Such benefit may be at least amelioration of one symptom. The actual amount administered, and rate and time-course of the administration, will depend on the aim of the administration, e.g. the biological effect sought in view of the nature and severity of the challenge and is the subject of routine optimization. Prescription of treatment, for example decisions on dosage etc., is within the responsibility of general practitioners and other medical doctors.

The compositions according to the invention are also useful in agriculture, horticulture, vegetable growing, ornamental plant cultivation, fruit growing, bulb growing, the culture of potted plants, forestry etc., and as consumer product for indoor plants. The present invention therefore also relates to a plant protection composition for controlling pathogenic bacteria, viruses, and/or fungi on plants and the like, in addition to a method wherein the composition is applied to the plant or plant part or a locus thereof. An advantage of the composition according to the invention is that the danger of resistances is very small or even absent.

The term "plant protection composition" as used herein refers to compositions for plant protection, such as bactericide composition, virucide composition or fungicide composition which can be applied to plants or soil to protect or treat plant or plant products against all harmful organisms or prevent the action of such organisms.

A "plant" as used herein encompasses a plant cell, plant tissue (including callus), plant part, whole plant, ancestors and progeny. The term "plant also encompasses all plants and plant populations such as desired and undesired wild plants or crop plants (inclusive of naturally occurring crop plants). Crop plants can be plants which can be obtained by conventional plant breeding and optimization methods or by biotechnological and recombinant methods or by combinations of these methods, inclusive of the transgenic plants and inclusive of the plant cultivars protectable or not protectable by plant breeders' rights. A plant part may be any part or organ of the plant and include for example a seed, fruit, fruit body, stem, leaf, needle, stalk, shoot, flower, anther, root, tuber or rhizomes. The term "plant" also encompasses vegetative and generative material for example cuttings, tubers, rhizomes, offsets, seeds, suspension cultures, embryos, meristematic regions, callus tissue, gametophytes, sporophytes, pollen, and microspores. The plant as used herein refers to all plants including algae, ferns and trees. The composition and the method according to the invention can be used in the broadest sense for plant protection and pathogen control in for instance agriculture, horticulture, vegetable growing, ornamental plant cultivation, fruit growing, bulb growing, the culture of potted plants, forestry etc., and as consumer product for indoor plants. In addition to the plants themselves, plant parts can also be treated such as bulbs, tubers, flowers, cuttings, fruits and the like. In addition to the plants and part thereof themselves, the locus of the plant can be treated.

The term "locus" as used herein encompasses the environment or habitat of the plant to be protected, for example the place on which the plants are growing, where the seeds of the plants are sown or where the seeds of the plants will be sown. An example for such a locus is soil such as a field, on which plants are growing. According to an embodiment of the invention, the composition can be applied to soil and the method is used to control plant parasitic organism that are located in the soil. This treatment may occur before planting or after planting.

In an embodiment, the composition according to the present invention, and for use in accordance to the present invention, is particularly useful for treating pre-harvest and post-harvest crops contaminated by several micro-organisms.

The present invention is particularly useful for the control or the inhibition or micro-organism selected from fungi and bacteria. For example said composition is particularly useful against *Penicillium* spp.; *Botryotinia* spp. such as *Botrytis cinerea*; *Didymella* spp. such as *Didymella lycopersici* and *Didymella bryonia*; *Pythium* spp.; *Plasmopara* spp.; *Peronospora* spp.; *Sclerospora* spp.; *Sphaerotheca* spp. such as *Sphaerotheca pannose* and *Sphaerotheca fulisinea*; *Puccunia* spp. such as *Puccunia horiana*; *Erysiphe* spp.; *Oidium* spp.; *Leveillula* spp. such as *Leveillula taurica*; *Fusarium* spp.; *Phytophtora* spp.; *Rhizoctonia* spp.; *Verticillium* spp.; *Sclerotinia* spp.; *Rhizopus* spp. and *Ventura* spp. and the like.

Plant bacterial infections which can be treated with the composition according to the invention are inter alia infections by *Erwinia chrvsanthemi*, *Pseudomonas syringe*, *Xanthomonas camtestris*, and *Curtobactrium flaccumfaciens*.

The composition according to the invention can also be used in a mixture with known plant fungicides, or plant bactericides, to widen, for example, the activity spectrum or to further prevent the development of resistance.

The present invention also relates to method for preparing a plant protection composition as described herein, comprising the step of mixing—at least one ion selected from hypohalite, —at least one compound selected from lactoferrin, lactoferrin peptide, lysozyme, immunoglobulins or a combination thereof, —optionally hypothiocyanite, and —optionally at least one growth factor, with a surfactant or diluent normally used in plant protection compositions.

These plant protection compositions may be prepared in a manner known per se. For example, the composition can be converted into the customary formulations, such as solutions, emulsions, wettable powders, water dispersible granules, suspensions, powders, dusting agents, foaming agents, pastes, soluble powders, granules, suspo-emulsion concentrates, microcapsules, fumigants, natural and synthetic materials impregnated with the composition and very fine capsules and polymeric substances.

These formulations can be prepared in a known manner, for example by mixing the elements of the composition according to the invention with surfactant or diluent normally used in plant protection compositions such as for example mixing with extenders, that is liquid solvents, liquefied gas and/or solid diluents or carriers, if appropriate with the use of surface-active agents, that is emulsifiers and/or dispersants and/or foam-formers.

The composition can be applied by means of spraying, sprinkling, atomizing, overhead spraying, watering, immersing, drip irrigation and the like. The composition according to the invention can also be used to disinfect drip irrigation systems. It is also possible to immerse the product to be treated in a bath with the composition according to the invention.

The compositions of the present invention will be better understood by reference to the following examples, which are illustrative only and are not meant to be limiting in any manner.

Example 1

Production of OSCN⁻, or or OCl⁻ Ion

The peroxidase immobilized on a solid support is added to a beaker. $H_2O_2$ and $SCN^-$ or $I^-$ or $Cl^-$ or a mixture of two or three thereof is added.

The solid support can be sludge, glass beads or chromatographic cationic supports and the like. The enzyme can be covalently fixed. The enzyme can be ion ically fixed or fixed by absorption.

Once the reaction over, the mixture is settled and filtrated to remove the immobilized enzyme.

The filtrated solution contains $OSCN^-$ and/or $OI^-$ and/or $OCL^-$. As used herein these solutions will be referred as "$OSCN^-$ solution", "$OI^-$ solution", "$OCl^-$ solution", $OSCN^-/OI^-/OCl^-$ solution, $OSCN^-/OI^-$ solution, $OCl^-/OI^-$ solution, $OSCN^-/OCl^-$ solution. The solution may also contain unreacted substrate.

The hypohalite and/or hypothiocyanite ions produced herein have an activity against microorganism having sulfhydryl groups on their membrane. However, in the presence of its producing enzymatic system (continuous production) the ion can also react with the tyrosine presents in the proteins, enzymes and peptides present in the medium. Iodination of protein (marker) for tumor detection is known. The iodination mechanism is only possible with a peroxidase system and not with the $OI-$ alone.

The hypohalite and/or hypothiocyanite ions when together with their enzymatic production system tend to react not only with microorganisms but also with tyrosine present in molecules, which diminish the effective concentration of said ions.

When these ions are used without their enzymatic system, they only react on the microorganisms since the reaction with tyrosine is only catalyzed in the presence of the peroxidase.

The same phenomenon can be observed in the presence of unsaturated oils, which double bond can be saturated with the above mentioned ions only in the presence of their enzymatic production system. Such saturated oil presents a rancid taste. The saturation reaction does not happen when the ions are isolated and used without their enzymatic production system.

Another example of the difference of activity of the above mentioned ions when isolated can be shown with hemoglobin which can be oxidized only in the presence of peroxidase system. This phenomenon does not happen when the ions are used without their enzymatic producing system.

Example 2

Illustrative base formulations for pharmaceutically-acceptable carriers for the pharmaceutical composition of the present invention to be formulated as a topical medicament for topical administration, such as a cream, a gel or to be incorporated in a bandage or pad, are set forth in Table 1, as follows. The following table shows varying ingredients and prophylactic and therapeutic effective amounts (quantities) which can be used in the preparation of topical pharmaceutical composition according to an embodiment of the present invention.

TABLE 1

Unless otherwise provided the weights are given in grams

| Ingredients | A | B | C |
|---|---|---|---|
| OSCN⁻ (21.51% deionized water) | 250 µm | — | — |
| OI⁻ (21.51% deionized water) | — | 200 µM | — |
| OCl⁻ (21.51% deionized water) | — | — | 200 µM |
| Cirami N. | 20.0 | 20.0 | 20.0 |
| Sunflower Oil | 40.0 | 40.0 | 40.0 |
| Vitamin E | 0.04 | 0.04 | 0.04 |

TABLE 1-continued

Unless otherwise provided the weights are given in grams

| Ingredients | A | B | C |
|---|---|---|---|
| Tensami 4/07 | 2.0 | 2.0 | 2.0 |
| Tensami 1/05 | 3.0 | 3.0 | 3.0 |
| Bronopol | 2.0 | 2.0 | 2.0 |
| Myacide SP | 2.0 | 2.0 | 2.0 |
| Propylene Gylcol | 10.0 | 10.0 | 10.0 |
| Total | 100 | 100 | 100 |
| Lactoferrin | 0.5 g | 0.05 g | — |
| Lysozyme | 0.5 g | — | 0.05 g |
| immunoglobulins | 0.1 g | 0.05 g | 0.1 g |
| Growth factors | | | |
| Derived Platelet growth factor | 0.01 mg | 0.015 mg | 0.005 mg |
| Transforming growth factor | 0.005 mg | 0.0025 mg | 0.01 mg |
| Fibroblast growth factor | 0.015 mg | 0.01 mg | 0.005 mg |
| Epidermal growth factor | 0.015 mg | 0.01 mg | 0.005 mg |
| Angiogenin | 0.001 mg | 0.001 mg | 0.001 mg |

Cirami N.1, Tensami 4/07, Tensami 1/05, Bronopol and Myacide SP are all marketed by Alban Muller International, Montreuil, France.

Example 3

Illustrative formulations for pharmaceutically-acceptable carriers for the pharmaceutical composition of the present invention to be formulated as an eye wash solution for topical administration, as an eye drop or as an eye wash, are set forth in Table 2, as follows. The following Table shows the varying ingredients and the prophylactic and therapeutic effective amounts (quantities) which can be used in the preparation of eye wash medicaments, according to the present invention.

TABLE 2

Eye drop or eye wash (per 5 ml solution)

| Ingredients | | | |
|---|---|---|---|
| OSCN- (99.4% deionized water) | 250 µM | — | — |
| OI- (99.2% deionized water) | 250 µM | 200 µM | — |
| OCI- (98.1% deionized water). | — | — | 200 µM |
| Sorbic acid. (0.0025%) | 0.0002 | — | — |
| Boric acid | 0.018 | 0.018 | 0.018 |
| Sodium borate (hydrated 10H20) | 0.0015 | 0.0015 | 0.0015 |
| Sodium chloride | 0.0025 | 0.0025 | — |
| Benzalkonium chloride | 0.0001 | — | — |
| Edetate disodium | 0.001 | 0.001 | 0.001 |
| Total | 100 | 100 | 100 |
| Lactoferrin | 0.0005 g | 0.0005 g | — |
| Lysozyme | 0.0005 g | — | 0.0005 g |
| Immunoglobulins | 0.0001 g | 0.0001 g | 0.0001 g |
| Growth factors | | | |
| Derived Platelet growth factor | 0.001 mg | 0.0015 mg | 0.0005 mg |
| Transforming growth factor | 0.0005 mg | 0.00025 mg | 0.0001 mg |
| Fibroblast growth factor | 0.00015 mg | 0.0001 mg | 0.00005 mg |
| Epidermal growth factor | 0.00015 mg | 0.0001 mg | 0.00005 mg |
| Angiogenin | 0.00001 mg | 0.00001 mg | 0.00001 mg |

[1] The eye wash solution is a 5 ml solution of: 90 milligrams of Boric acid; 6.6 milligrams of hydrated sodium borate (10H20); 2500 units Vitamin A and 0.125 jug of sorbic acid 0.0025%

Example 4

Illustrative formulations for pharmaceutically-acceptable carriers for the pharmaceutical composition of the present invention to be formulated as an aqueous cream for cosmetic use are set forth in Table 3, as follows. The following Table 3 shows the varying ingredients and the prophylactic and therapeutic effective amounts (quantities) which can be used in the preparation of an aqueous cream, according to the present invention.

TABLE 3

| | | |
|---|---|---|
| Lactoferrin peptides | 10 mg | 10 mg |
| Bovine whey colostrum | 100 mg | 100 mg |
| Emulsifying wax | 9 g | 9 g |
| White soft paraffin | 10 g | 10 g |
| OSCN- (500 µM in purified water respectively) | to 100 g | to 100 g |
| 01-OSCN- (450 µM + 50 µM in purified water respectively) | | |

Example 5

Compositions according to the invention (Table 4) formulated as in example 3 were tested on planktonic bacteria and on bacteria organized in biofilms. The ration ATP content/microbial count of was measured. Reference compositions (7-10) were also tested. The results are shown in Table 5. The results are established by means of a notation scale, from 0 (no growth inhibition) to 5 (total growth inhibition). From 0 to 5.5 representing very good antimicrobial effect of the composition and 0 being no antimicrobial effect.

TABLE 4

| Compositions | 1 | 2 | 3 | 4 | 5 | 6 | 7 | 8 | 9 | 10 | 11 |
|---|---|---|---|---|---|---|---|---|---|---|---|
| OSCN- | + | | + | | + | | + | | | | |
| OI- | + | | + | | + | | + | | | | |
| OCI- | | + | | + | | + | | + | | | |
| Lactoferrin | + | + | + | + | + | + | | | + | + | + |
| Lysozyme | | + | | + | | + | | | | + | + |
| Immunoglobulins | + | | + | | + | | | | + | | + |
| Derived Platelet growth factor | + | | | | | | | | + | | |
| Transforming growth factor | + | | | | | | | | + | | |
| Fibroblast growth factor | | + | | | | | | | | + | |
| Epidermal growth factor | | + | | | | | | | | + | |
| Angiogenin | + | + | | | | | | | + | + | |
| whey colostrum | | | | | + | + | | | | | |
| Lactoperoxidase/ potassium thiocyanate/H202 | | | | | | | | | | + | + | + |

TABLE 5

| Composition | planktonic bacteria | bacteria organized in biofilm |
|---|---|---|
| 1 | 5 | 5 |
| 2 | 5 | 5 |
| 3 | 5 | 5 |
| 4 | 5 | 5 |
| 5 | 5 | ND |
| 6 | 5 | ND |
| 7 | 3 | 0 |
| 8 | 3 | 0 |
| 9 | 3 | 4 |

TABLE 5-continued

| Composition | planktonic bacteria | bacteria organized in biofilm |
|---|---|---|
| 10 | 3 | 4 |
| 11 | 3 | 0 |

ND: no date yet.

Example 5

Figure 1:
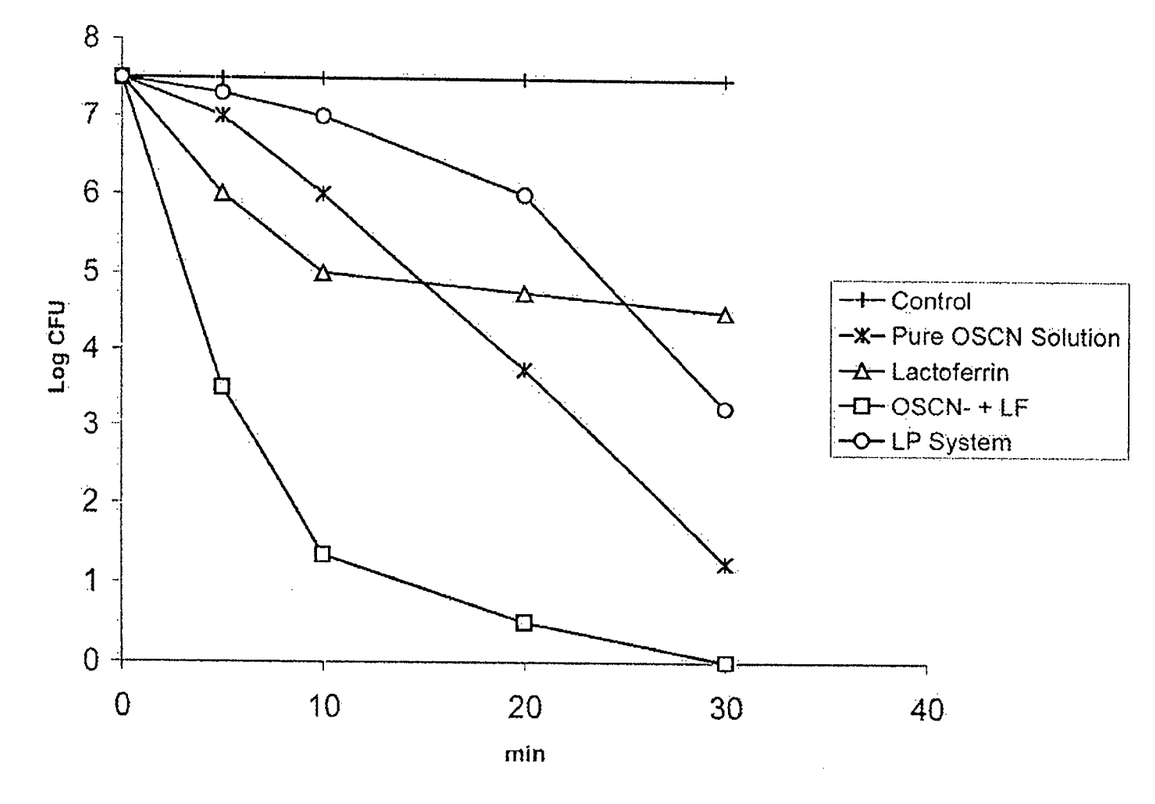
FIG. 1 represents a graph comparing the activity (Log Cfu/min) of a solution according to an embodiment of the invention against solutions of the art.

A solution comprising OSCN⁻ and lactoferrin was tested against *Helicobacter pylori*, and its activity was compared to a solution comprising lactoferrin alone, a solution comprising OSCN⁻ alone, a solution comprising the lactoperoxidase system and a control. The same component concentrations were tested for each solution. The results are shown under FIG. 1 and are expressed in Log CFU/min. The graph of FIG. 1 shows that the solution comprising lactoferrin and OSCN- is more active on bacterial count than lactoferrin alone or OSCN⁻ alone. It can be seen that there is a synergetic effect of the composition comprising lactoferrin and OSCN⁻ compared to the solutions comprising the components alone.

Example 6

Composition according to an embodiment of the invention was formulated as the formulation 5 of the Table 4.

The antimicrobial activity of the formulation has been evaluated by a diffusion test. A suspension of the *Sphaerotheca pannose* in Sabouraud broth (OXOID CM147, Basingstoke, UK) was adjusted to an absorbance (600 nm) of 0.8 on a spectrophotometer Beckman corresponding to 1.55+/−0.32 $10^7$ CFU/ml. Standardized inoculums (25 µl) of the suspension were swapped onto the surface of Sabouraud plates centrally gel-punched (diameter: 15 mm) and then 1 ml of the formulation was deposited in the central well. Microcolonies were evident after 24 h at 37° C. but the lawn of growth was confluent or nearly confluent after 48 h. After 2 days incubations at 37° C., the radius of the inhibition zone at the agar surface was measured around the central well in four orthogonal directions.

Petri dishes gel-punched and plates were inoculated with *Sphaerotheca pannose* after 48 hours incubation at 37° C. in the presence of the formulation 5 and one Petri dish was used as control, inhibiting the formulation at 85° C. during 6 hours. A circle free of the micro-organisms was clearly visible between the central well containing the formulation. The inhibition radius after 48 hours incubation was 7.9 mm+/−2 mm in the case of the formulation 5 and 0 mm in the case of the control, that meant no inhibition of the micro-organism after heating the formulation at 85° C. since the confluent *Sphaerotheca pannose* lawn touched the limit of the well filled with inactivated product.

What is claimed is:

1. A composition comprising:
   isolated hypothiocyanite ions not in combination with a peroxidase system; and
   at least one compound selected from the group consisting of lactoferrin, lactoferrin peptide, and combinations thereof.

2. The composition according to claim 1, further comprising isolated hypohalite ions not in combination with a peroxidase system.

3. The composition according to claim 2, wherein said hypohalite ions are selected from hypochlorite, hypoiodite, hypobromite, and combinations thereof.

4. The composition according to claim 1, wherein said at least one compound is lactoferrin.

5. The composition according to claim 1, further comprising a growth factor selected from the group consisting of platelet derived growth factor, fibroblast growth factor, transforming growth factor, angiogenin, epidermal growth factor and combinations thereof.

6. The composition according to claim 5, wherein the composition comprises colostrum as a source for said at least one growth factor.

7. The composition according to claim 1, further comprising a compound selected from the group consisting of triclosan, chlorhexidine, cetylpyridunium, and combinations thereof.

8. The composition according to claim 1, wherein said isolated hypothiocyanite ion is in a concentration ranging from 0.1 µM to 5000 µM.

9. The composition according to claim 2, wherein said at least one hypohalite ion is in a concentration ranging from 0.1 µM to 5000 µM.

10. A composition comprising:
    isolated hypothiocyanite ions not in combination with a peroxidase system; and
    lactoferrin in a concentration ranging from 0.1 µg to 5000 mg/l.

11. A composition comprising:
    isolated hypothiocyanite ions not in combination with a peroxidase system; and
    lactoferrin peptide in a concentration ranging from 0.1 µg to 5000 mg/l.

12. The composition according to claim 1, wherein said composition is in a fluid form.

13. A pharmaceutical or plant protection composition comprising the composition according to claim 1, and a pharmaceutically or plant protection acceptable carrier.

14. A method for preventing or treating diseases selected from the group consisting of gastro-intestinal infections, calculus and occurrence of caries, gingivitis, mucositis, periodontal diseases, vaginal diseases, herpes, acne, ulcers, traveller's diarrhea, cystitis, molluscum contagiosum, and *chlamydia* infections, comprising:
    administering to an individual in need thereof the composition according to claim 1.

15. A method for prophylaxis and therapy of infectious diseases caused by microorganisms present in biofilms adherent to cell surfaces comprising:
    administering to an individual in need thereof the composition according to claim 1.

16. The method according to claim 15, wherein said microorganisms are selected from the group consisting of bacteria, viruses, protozoas, yeast, fungi, and parasites.

17. The method for controlling plant-pathogenic bacteria and/or fungi on plants, and on parts or a locus thereof, comprising:
    applying to the plant, or part or a locus thereof the composition according to claim 1.

* * * * *